United States Patent [19]

Roberts

[11] Patent Number: 4,547,158

[45] Date of Patent: Oct. 15, 1985

[54] DENTURE SUPPORT FRAME

[76] Inventor: Harold D. Roberts, 8115 Adera, Vancouver, B.C., Canada, V6P 5E4

[21] Appl. No.: 627,079

[22] Filed: Jul. 2, 1984

[51] Int. Cl.$^4$ ............................................... A61C 8/00
[52] U.S. Cl. ..................................................... 433/176
[58] Field of Search ................................. 433/173, 176

[56] References Cited

U.S. PATENT DOCUMENTS

| | | | |
|---|---|---|---|
| 1,140,538 | 5/1915 | Skinner | |
| 3,577,853 | 5/1971 | Roberts | 32/10 |
| 3,641,671 | 2/1972 | Roberts | 32/10 A |
| 3,738,004 | 6/1973 | Edelman | 32/10 A |
| 3,908,269 | 9/1975 | Christenot | 32/10 A |
| 4,062,119 | 12/1977 | Linkow et al. | 32/10 A |
| 4,202,099 | 5/1980 | Roberts | 433/176 |
| 4,377,382 | 3/1983 | Roberts | 433/176 |

*Primary Examiner*—Robert Peshock
*Attorney, Agent, or Firm*—Eugene M. Eckelman

[57] ABSTRACT

A one-piece U-shaped bar is arranged to support an artificial denture on its upper edge and terminates at the rearward end in ramus implants. Each of the ramus implants comprises a rear extension of side portions of the bar, and these extensions are of reduced thickness than other portions of the bar for fitting between narrowed side defining bone areas of ramus portions of the jaw. Rear extensions of the bar are offset laterally for proper fitting in the ramus portions of the jaw. The rear extensions have apertures therethrough with funnel shaped openings at the sides for providing a locking connection of bone growing through the openings.

4 Claims, 4 Drawing Figures

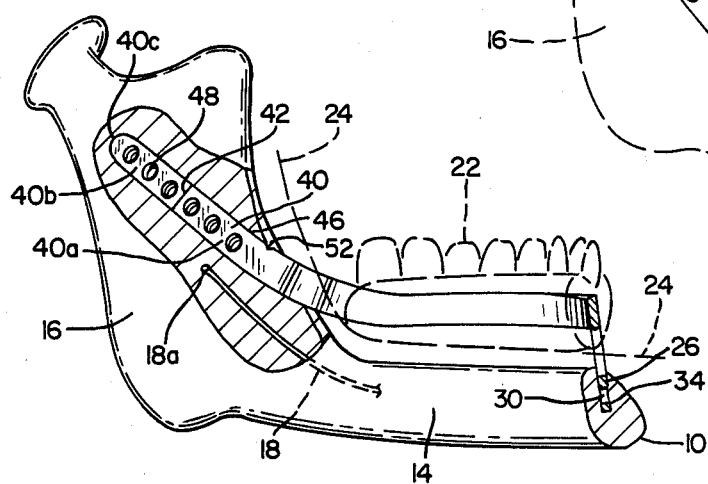
FIG. 1
FIG. 2
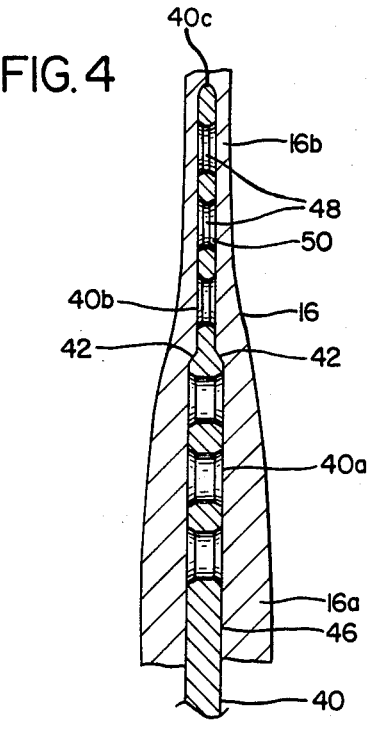
FIG. 4
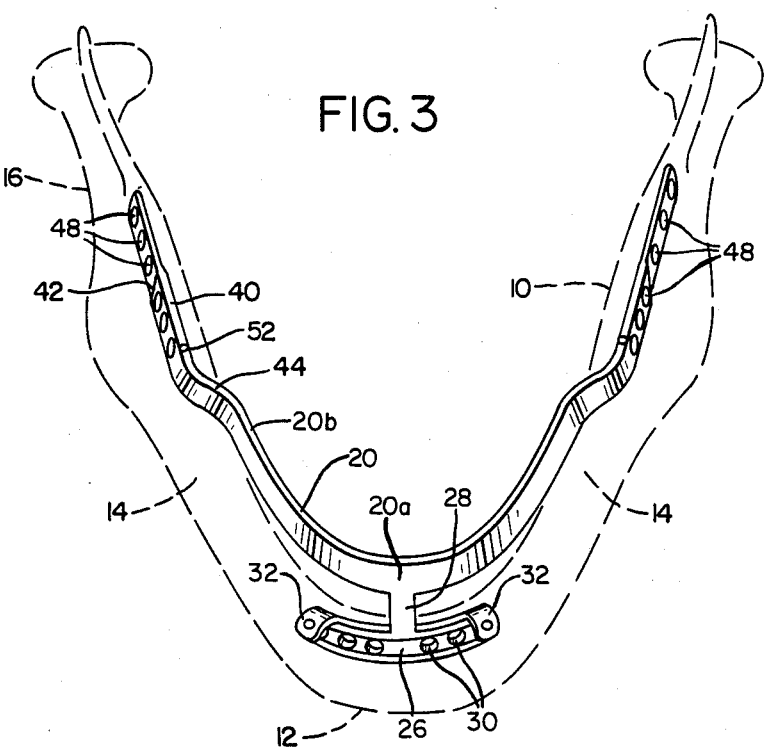
FIG. 3

DENTURE SUPPORT FRAME

BACKGROUND OF THE INVENTION

This invention relates to new and useful improvements in denture support frames of the type which include implants set in the mandible or lower jaw bone of a person.

Denture support frames have heretofore been provided which employ a one piece bar having substantially the contour of the mandible as viewed in plan and having rear extensions implanted into the ramus portions of the mandible. In the formation of this bar-type denture support, it is desired that the bar have a solid support in the ramus portions of the mandible and also that it have a structure which will not pivot in the bone or deflect to the extent that the implants will loosen due to stresses of mastication. In order to achieve a most favorable implant in the ramus portions of the jaw bone, it is desirable that the rear extension penetrate as far as possible into the ramus portion. In view of the front to rear structure of the ramus portion, however, these implants have had substantially short penetration. More particularly, while the forward end of the ramus portions are quite wide and the support bar or implant portions can be readily set therein, the rearward end thereof tapers together to a substantially thin structure and it has not been deemed possible to utilize such rearward end as an implant area. This is particularly true since the majority of implants are in persons of advanced age and the bone usually has some atrophy. Such prior implants have only penetrated the widened forward part of the ramus portions.

SUMMARY OF THE INVENTION

According to the present invention and forming a primary objective thereof, a denture support frame is provided which provides an improved support of denture support bars in a mandible and more particularly a support frame having a novel terminal end portion which is designed to be implanted in the thinned rearward end of the ramus portion, thus adding to the efficiency of implant connection of ramus implants heretofore utilized. Another object of the invention is to provide a particular shape of denture support bar that contributes to the novel implant arrangement in the ramus portion of the mandible and also to minimize food compaction in side areas of the mouth.

In carrying out the objectives of the invention, a one-piece U-shaped bar has upper and lower edges and is arranged to support an artificial denture on its upper edge. The bar has front and rear portions with the front being curved similar to the front curvature of the mandible and the rearwardly extending portions at the sides following substantially the contour similar to the sides of the mandible. Each of the rearward ends of the bar includes an extension which terminates in a free thinned end arranged for penetration into the ramus portions of the mandible. These thinned ends are forced or partially forced into the bone of the ramus portion during installation thereof and such thickness dimension is such that it will fit in an area otherwise not heretofore penetrated by implants, thus providing a stronger connection between the implant and the mandible than heretofore accomplished. The rear extensions angle upwardly from the side portions of the bar at a selected angle for accomplishing the elongated implant area, and furthermore these rear extensions are offset laterally outwardly from the side portions of the bar for proper fitting in outer bone areas of the ramus portions. The implant portions have apertures therethrough with funnel-shaped openings at the sides for providing a locking connection with bone growth.

The invention will be better understood and additional objects and advantages will become apparent from the following description taken in connection with the accompanying drawings.

BRIEF DESCRIPTION OF THE DRAWINGS

FIG. 1 is a perspective view of the present denture support frame, a mandible in which the frame is mounted being shown in broken lines;

FIG. 2 is a fragmentary side elevational view of the denture support frame and a mandible, a portion of the mandible being broken away to show an implant portion of the invention installed therein;

FIG. 3 is a front perspective view of the support frame, the mandible being shown in broken lines, and FIG. 4 is an enlarged fragmentary sectional view of the support frame taken on the line 4—4 of FIG. 1.

DETAILED DESCRIPTION OF A PREFERRED EMBODIMENT

With particular reference to the drawings, the numeral 10 represents a lower jaw bone or mandible of a person. The forward portion 12 of the mandible is curved and the sides 14 extend from such curvature in substantially a straight line to ramus portions 16. Ramus portions 16 comprise rearward longitudinal extensions of the sides but also extend vertically for hinged connection to the skull. The outer surface portions of the mandible, including the ramus portions, consist of hard corticle-type bone and the interior thereof consists of spongy-type bone. As best seen in FIG. 4, the front area 16a of the ramus portions are rather wide but such ramus portions taper to a thin area 16b at the rear. The alveolar nerve 18 enters the ramus portions at about halfway between the top and bottom, designated by the numeral 18a, and extends around the mandible.

The present invention comprises a rigid U-shaped denture support bar 20 which extends along the upper ridge of the mandible. As is customary in the use of this type of denture support frame, the natural teeth have all been removed and the bar 20 is arranged to support a full artificial denture 22 which is firmly but removably seated on the bar in a known manner into comfortable contact with or in close proximity to the gum surface. The gum surface is designated by the reference numeral 24 in FIG. 2. The present invention is used primarily on mandibles having severe damage or atrophy wherein surface support of dentures is not practical. In such damage or atrophy, the ramus portions 16 also have less bone area and the present invention was conceived to accommodate such cases.

The denture support bar 20 is shaped from end to end to conform to the shape and size of the mandible and to overlie the latter, namely, it has a curved front portion 20a similar to the curved portion 12 of the mandible and it has substantially straight side portions 20b conforming to the substantially straight side portions 14 of the mandible. The bar is provided with an integral downwardly extending frontal implant blade 26 supported at the central forward portion by a depending post 28. The blade 24 has a plurality of holes 30 therein which allow for bone growth, and preferably such blade is also provided with forwardly directed tabs 32 which seat on the mandible to provide firm support. The supporting post 28 for the blade 26 angles forwardly from the bar a slight amount and is fitted in a similarly angled recess 34 cut in the front portion of the mandible. This recess is cut to conform substantially to the angle of the mandible at the front with consideration given to damage or atrophy of the mandible to accomplish the best attachment to the bone.

The bar 20 has rear extensions 40 which lead integrally rearwardly from the side portions 20b of the bar 20 at an upwardly directed angle. A preferred angle a between these rear extensions 40 and the sides 20b of the bar is approximately 20 degrees. Each of the rear extensions 40 comprises two implant sections consisting of a first section 40a and a second rearward terminal end section 40b, this latter section having a length up to about 15 mm. The section 40a comprises a continuance of the bar 20 as to thickness, namely, approximately 2 mm., and the section 40b comprises a thinner dimension, namely, approximately 1 mm. Section 40b terminates at its free end in a rounded edge 40c. The juncture between the sections 40a and 40b preferably is sharply defined to provide upright shoulder portions 42. The rear extension 40 is offset outwardly relative to the sides 20b of the bar by an offset portion 44 of the bar.

For the purpose of installing the rear extensions 40 in the ramus portions 16, recesses 46 are first cut to the length of the sections 40a plus a very short distance upwardly past the point of installation for the purpose of maneuvering the front implant portion 26 in its recess 34. When inserting the rear extensions 40, they are directed into their respective recesses 46 and then the bar is forcefully driven rearwardly to drive the thin end sections 40b into the soft bone of the mandible, the rounded edge 40c serving to push through the bone in this step of the process. Upon reaching the recess 34 at the front with the implant portion 26, the latter can be inserted in its recess and the entire bar shifted slightly forwardly to seat this front implant portion. This will leave a short space in the bone at the upper end of the implant portion 40b but such portions, being in soft bone, will heal quickly. A tool is preferably employed for partially forcing a path for the thinned sections 40b prior to installation of the latter, such tool being the subject matter of my copending application Ser. No. 625,214 filed June 27, 1984.

Thus, the ramus implant portions 40 when installed comprise the sections 40a installed in cut recesses and the sections 40b installed in areas that have been forced open either by themselves or by a special tool. The sections 40a and 40b, being installed in soft bone of the mandible quickly receive bone growth therearound for positive connection. In a preferred arrangement, these implant portions have holes 48 in both the sections 40a and 40b to which bone grows in healing. Also in a preferred construction, these holes have funnel-shaped tapers 50 at their openings which assist in providing locking bone growth to the implant portions.

According to the invention, the sharp upward angle a and the substantially elongated dimension of the extension provides a positive implant connection to the ramus portions of the mandible. The offset 44 serves both to lead the rear extensions properly into the ramus portions for centering the sections 40b precisely between the sides of the thinned portion 16b and also to provide clearance for mouth tissue at the sides. As apparent in FIG. 4, the rear part 16b of the ramus portions is too narrow to receive the full width of the bar 20, but with the thinned section 40b, such thinned section can be installed in this rear part of the ramus portions to take advantage of the additional bone structure for securement of the implants. Although in some cases the rear part 16b of the ramus portions may have sufficient width to receive the full thickness of the bar 20, such is not usually the case, particularly in view of the fact that as stated above the present invention is used primarily on persons having the usual atrophy of the bone structure. With the present structure of bar, a fit can be accomplished in substantially all cases.

The upwardly angled rear extensions 40 thus comprise substantially straight extensions of the sides of the bar, except for the slight offset 44, and also have approximately the same edgewise disposition, thus making a structure which is not springy or otherwise subject to flexure. The only exit of the support bar at the ramus portions will be the bar itself and the gum tissue will quickly heal around this bar so that there will be minimum chance of infection and food compaction.

Notches 52 are cut in the top edge of the bar at the extensions 40 to guide the dentist in the amount of penetration of the implants into the ramus portions of the mandible.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A denture support frame arranged to be secured to the lower jaw of a person for supporting an artificial denture thereon, said frame comprising a one-piece U-shaped bar having upper and lower edges and arranged to support an artificial denture on its upper edge, said bar having front, side and rear portions with the front being curved to conform to the front curvature of the jaw and the side portions extending rearwardly in vertical alignment with the sides of the jaw bone whereby said front and side portions are of a contour similar to the contour of the lower jaw of a person, said front and side portions being arranged to overlie the lower jaw in substantially parallel relation thereabove, a rear ramus implant portion on each side of said bar arranged to be implanted in recesses cut in the ramus portions of the jaw bone, each of said ramus implant portions comprising an upwardly angled rear extension of said side portions and having first and second portions with said second portion terminating in a free end arranged for penetration into ramus portions of the jaw, said second portion of said rear extensions being substantially thinner than other portions of said bar for between narrow side defining bone areas of ramus portions of a jaw, and front support means on said bar arranged for engagement with the jaw said first portion of the upwardly angled rear extensions having a thickness of approximately 2 mm. and said second portion thereof having a thickness of approximately 1 mm.

2. The denture support frame of claim 1 wherein said rear extensions are offset laterally outwardly from said side portions for said proper fitting between opposite outer bone portions of ramus portions of a jaw.

3. The denture support frame of claim 1 wherein said rear extensions angle upwardly from said side portions at approximately a 20 degree angle.

4. The denture support frame of claim 1 wherein said thinned portions of said bar are approximately 15 mm in length.

* * * * *